United States Patent [19]

Young et al.

[11] Patent Number: 4,855,528

[45] Date of Patent: Aug. 8, 1989

[54] CATALYSTS AND PROCESS FOR OLIGOMERIZATION OF OLEFINS WITH NICKEL-CONTAINING ZEOLITE CATALYSTS

[75] Inventors: David A. Young, Baton Rouge, La.; David E. Vaughan, Flemington, N.J.; Roy L. Pruett, Harrisburg, N.C.; Mafer E. Tunison, Baton Rouge, La.

[73] Assignee: Exxon Chemical Patents Inc., Linden, N.J.

[21] Appl. No.: 153,707

[22] Filed: Feb. 5, 1988

[51] Int. Cl.$^4$ ............................ C07C 2/10; C07C 2/12
[52] U.S. Cl. ...................................... 585/531; 585/533
[58] Field of Search ............... 585/407, 418, 422, 430, 585/431, 531, 533, 520, 419, 417

[56] References Cited

U.S. PATENT DOCUMENTS

| 3,402,217 | 9/1968 | Engelbrecht et al. | 585/531 |
|---|---|---|---|
| 3,960,978 | 6/1976 | Givens et al. | 585/531 |
| 4,029,719 | 6/1977 | Forni et al. | 585/533 |
| 4,309,313 | 1/1982 | Barrett et al. | 502/60 |
| 4,417,087 | 11/1983 | Miller | 585/530 |
| 4,456,527 | 6/1984 | Buss et al. | 258/89 |
| 4,465,884 | 8/1984 | Degnan et al. | 585/431 |
| 4,531,014 | 7/1985 | Gregory et al. | 585/407 |
| 4,542,251 | 9/1985 | Miller | 585/533 |
| 4,551,438 | 11/1985 | Miller | 502/62 |
| 4,628,138 | 12/1986 | Barnett et al. | 585/531 |
| 4,665,250 | 5/1987 | Chu et al. | 585/533 |
| 4,740,652 | 4/1988 | Frame | 585/531 |

*Primary Examiner*—Anthony McFarlane
*Attorney, Agent, or Firm*—J. J. Mahon

[57] ABSTRACT

There are disclosed catalysts and process for oligomerizing $C_3$–$C_{12}$ olefins in the liquid phase at 50° C.–150° C. in the presence of a nickel containing zeolite catalyst, the zeolite being a Cs or Ba exchanged CSZ-1, high silica ultra-stable faujasite and zeolites isostructural with mazzite.

13 Claims, No Drawings

CATALYSTS AND PROCESS FOR OLIGOMERIZATION OF OLEFINS WITH NICKEL-CONTAINING ZEOLITE CATALYSTS

This invention relates to an improved liquid phase process for the oligomerization of olefins having about 3 to 12 carbon atoms and certain zeolite catalysts useful therefor.

More particularly this invention relates to a liquid phase oligomerization process for preparing oligomers of olefins such as propylene and butene at moderate temperatures in the liquid phase using nickel-containing synthetic zeolites such as CSZ-1, high silica faujasites and zeolites isostructural with mazzite.

In general the use of nickel-containing catalysts to effect the oligomerization reaction of olefins is known. It is also known to use certain types of nickel-containing zeolites. The present invention is based upon the discovery that nickel-containing CSZ-1, high silica faujasite and mazzite-like zeolites are highly effective and provide greater yields of oligomerized products in a relatively shorter reaction period than prior art catalysts.

U.S. Pat. No. 4,309,313, issued Jan. 9, 1982 to Barrett et al. describes CSZ-1 zeolites and their manner of preparation. It further discloses that the zeolites are useful as hydrocarbon conversion catalysts for cracking and aromatization processes. This patent describes CSZ-1 which is used in the present invention.

U.S. Pat. No. 3,402,217, issued Sept. 17, 1968 to Engelbreckt et al. discloses that use of NiO and 13X zeolite for oligomerizing propylene to hexenes. However, a very low catalyst efficiency is reported.

U.S. Pat. No. 4,029,719, issued June 14, 1977 to Forni et al. also discloses nickel 13X zeolites as olefin oligomerization catalysts but requires pre-treatment of the catalyst with organic or inorganic base prior to use.

U.S. Pat. No. 4,542,251, issued Sept. 17, 1985 to S. J. Miller discloses liquid phase oligomerization of $C_2$ to $C_{20}$ olefins with nickel-containing HZSM-5, HZSM-11 zeolites and mixtures thereof at temperatures in the range of 45° F. to 450° F.

U.S. Pat. No. 4,551,438, issued Nov. 5, 1985 to S. J. Miller discloses the use in olefin oligomerization of nickel-containing ZSM-5, ZSM-11, silicalite or CZM zeolite, wherein the zeolite is treated with a hydrocarbyl aluminum halide.

U.S. Pat. No. 3,325,465, issued June 13, 1967 to Jones et al. contains a broad disclosure of the use of aluminosilicate catalysts containing nickel or cobalt for use in the polymerization of olefins.

U.S. Pat. No. 3,960,978, issued June 1, 1976 to Givens et al. discloses the use of nickel-containing ZSM-5 and ZSM-11 zeolite for oligomerizing olefins useful for gasoline blending at reaction temperatures of 500° F. to 900° F.

U.S. Pat. No. 3,827,968, issued Aug. 6, 1974 to Givens et al. describes a two stage process for oligomerization and aromatization using a ZSM-5 zeolite which may contain nickel.

U.S. Pats. Nos. 4,628,138 and 4,628,139, both issued Dec. 9, 1986 to Barnett et al. and K. W. Barnett, respectively, disclose omega zeolites, which are isostructural with mazzite, formed by either reducing a nickelocene on the zeolite or depositing a cyclooctadiene Ni(O) onto the zeolite. The only specific disclosures relate to the oligomerization of ethylene.

The present invention is distinguished from the foregoing references in that the nickel-containing zeolites of this invention are different from those disclosed in the prior art references and provide a degree of catalyst activity and selectivity not found in prior art processes for oligomerizing propylene and higher olefins.

In accordance with the present invention there has been discovered a process for oligomerizing $C_3$–$C_{12}$ olefins which comprises contacting a $C_3$–$C_{12}$ olefin, or mixtures thereof, in the liquid phase at a temperature of about 50° C. to about 150° C. with a calcined, nickel-containing zeolite catalyst, the nickel being added in an effective amount either by cation exchange or by impregnation, the zeolite being selected from the group consisting of cesium-exchanged and barium-exchanged CSZ-1, ultrastable high silica faujasite and zeolites having a structure generally similar to mazzite or isostructural with mazzite. The nickel-containing zeolite catalysts per se are considered to be novel compositions of matter and as such constitute a further embodiment of the present invention.

The terms oligomerization and oligomers as used herein are employed in their normal sense and refer to polymerization wherein the degree of polymerization is about two to five although somewhat higher molecular weight oligomers can also be formed in the reaction. A preferred aspect of the present invention is to prepare dimers, trimers, tetramers and pentamers of propylene, butene-1 and butene-2.

The first category of catalysts of this invention are the zeolites categorized as CSZ-1 which are cesium-exchanged or barium-exchanged as well as nickel-containing. This type of zeolite was first disclosed in U.S. Pat. No. 4,309,313 issued to Barrett et al. Those useful in this invention may have a composition 0.05 to 0.55 cesium:0.45 to 0.95 $Na_2O:Al_2O_3$: 3 to 100 $SiO_2$:X $H_2O$ where X is 0 to 10. The foregoing ratios include the high silica forms of CSZ-1.

To prepare the nickel-containing CSZ-1 zeolite useful in the present invention the CSZ-1 is cation exchanged with either cesium or barium cations and then nickel is added using either simple impregnation or further cation exchange.

Generally, the catalyst of this invention will contain about 0.2 to about 20% by weight nickel and preferably about 1 to 15% by weight nickel. Nickel is added by contacting the zeolite with an aqueous solution of a nickel salt. While a wide variety of nickel salts are useful, it is preferred to use chlorides or nitrates.

The other types of novel nickel-containing zeolite catalysts useful in the present invention are high silica "ultra-stable" faujasites and mazzite-like zeolites.

High silica faujasites are those faujasite zeolites having a high silica:alumina ratio, i.e., $SiO_2:Al_2O_3$ ratios of at least about 4.0. The Si:Al ratios of a variety of readily synthesized NaY materials can be increased by a wide range of chemical or physical chemical treatments. These processes involve removal of Al from the zeolite framework and creation of a metastable defect structure followed by filling the defects with Si from another part of the structure by further chemical treatments or hydrothermal annealing. Typical treatments use steam, e.g., U.S. Pat. No. 3,293,192; acid leaching, e.g., U.S. Pat. No. 3,506,400; treatment with EDTA, e.g., U.S. Pat. No. 4,093,560; treatment with $SiCl_4$ as disclosed by Beyer et al. in *Catalysis by Zeolites*, p. 203 (Elsevier Press; 1980) or treatment with $CHF_3$ as in U.S. Pat. No. 4,275,046 or other chemicals. These products are also referred to as "ultra-stable" because of their very high thermal and hydrothermal stability resulting from the replacement of $Al^{3+}$ by $Si^{4+}$ in the zeolite lattice.

The other methods of so called secondary synthesis using $(NH_4)_2SiF_6$ in aqueous solution have also been demonstrated to yield high silica faujasites as in U.S. Pat. No. 4,503,023. Directly synthesized high silica faujasites such as ECR-4 and ECR-32 or modifications thereof are also useful substrates.

A steamed, ultra-stable faujasite is prepared as follows: 100 gms. NaY faujasite commercial zeolite (Si/Al=2.4) was exchanged with a 10 wt. % solution of $NH_4Cl$ at 60° C. for one hour with stirring. The slurry was filtered, washed with one liter of distilled water and the filter cake was exchanged a second time with $NH_4Cl$ in a procedure identical with the first exchange. After filtering and washing the second time, the product was dried at 100° C. for one hour, then steam calcined in a closed crucible for three hours at 600° C. The product was exchanged two more times with $NH_4Cl$ at which time the $Na_2O$ level was about 0.5 wt. %. ELZ-20 is a commercially available form of this material from Union Carbide Corp. Steamed, ultra-stable Y faujasites are also identified in U.S. Pat. No. 3,293,192, issued Dec. 12, 1966 and are manufactured by W. R. Grace and Company.

Mazzite is a rare mineral and a naturally occurring zeolite; see Galli, Crystal Struct. Comm., 3 (1974), pp. 339-344. Isostructural forms of mazzite include ZSM-4, disclosed in British Patent No. 1,178,186, and zeolite omega, disclosed in British Patent No. 1,117,568, which differ only in Si/Al ratios and cation contents; see Meier et al., Atlas of Zeolite Structures (1978).

Zeolite omega has the following chemical composition on an anhydrous basis and has been designated ELZ-omega-5 by Union Carbide Corporation:
$Al_2O_3$: 15.49 wt. %
$SiO_2$: 77.12 wt. %
$Na_2O$: 6.44 wt. %
$SiO_2/Al_2O_3$: Molar Ratio 8.6
$Na_2O/Al_2O_3$: Molar Ratio 0.68

The process of this invention is carried out by contacting the catalyst with the olefin to be oligomerized under a pressure adequate to maintain the reactant in the liquid phase at the reaction temperature and intimately mixing the catalyst and olefin as the reaction proceeds.

A particular advantage of the present invention is that the catalysts exhibit a high turnover number (TON) which is defined as the moles of olefin converted per mole of nickel per hour. TON values of at least 25 are obtained in accordance with this invention. When using a preferred nickel-containing barium-exchanged CSZ-1 catalyst in accordance with the invention, a TON value of 175 moles of olefin converted was obtained. In contrast, when TON values are computed based on the disclosure of U.S. Pat. Nos. 3,402,717, 4,029,719, 4,542,251 and 4,551,438, TON values per hour for butene and propylene were about 9 to 18; these prior art patents disclose the use of nickel-containing zeolite catalysts for olefin oligomerization.

TON values are computed by calculating the moles of olefin which are converted, determining the moles of nickel present in the catalyst used and dividing the moles of olefin converted by the moles of nickel present and dividing that value by the number of hours the reaction was run.

Thus, for U.S. Pat. No. 3,402,717 the TON for Example 1 was calculated from the following data:
Rate of feed=1.25 g/hr/g catalyst
Catalyst is 3% by weight Ni
Feed is 80% propylene, 20% propane
Propylene rate of feed=1.0 g/0.03g Ni/hr
20% of propylene was converted
Propylene converted=0.2 g/0.03 g Ni/hr=0.0048 moles propylene/0.0052 moles Ni/hr=9.3 moles propylene/mole Ni/hr Thus, the TON value for this catalyst was 9.3.

A similar calculation was made for Example 2 of U.S. Pat. No. 4,029,719. for this calculation, the catalyst density was estimated at 1.5. The calculation was done as follows:
Example 2, Feed butene-1, 2 volumes/volume catalyst/hr density of butene=0.6, density of catalyst estimated as 1.5
feed=0.6×2 gms butene/1.5×1 gm catalyst/hr=1.2 gms butene/1.5 gms catalyst/hr
catalyst is 5% Ni
feed=1.2 gms butene/(1.5×0.05=0.075) gm Ni/hr
Product 79.2% conversion
0.792×1.2=0.95 gm butene converted/0.075 gm Ni/hr=0.95/56 moles butene converted/0.075/58 moles Ni/hr=0.017 moles butene converted/0.0013 moles Ni/hr TON=13/hr For U.S. Pat. No. 4,542,251, the TON was calculated for Example 6 as follows:
Example 6 gives highest rate with Ni catalyst 98% conversion, LHSV=0.5 (liquid hourly space velocity)
Catalyst 3 wt. % Ni
Density of propylene=0.6, density of catalyst assumed 1.5
Feed
0.5 ml propylene/1.5 gm catalyst/hr
0.3 gm propylene/0.045 gm Ni/hr
0.0071 moles propylene/0.00078 mole Ni/hr
rate=9.2 TON/hr Also, for U.S. Pat. No. 4,551,438, a TON value of 18.4 was computed based on the data of Example 5.

U.S. Pats. Nos. 4,628,138 and 4,628,139 disclose the use of zeolite catalysts containing nickel for ethylene oligomerizations and very high TON values, 1766 and 5860, were computed for the ethylene reactions disclosed in these references. However, TON values for ethylene catalysis are not comparable with catalysts for higher olefins oligomerization.

The process of the present invention is preferably employed to oligomerize propylene, butene-1 and butene-2 at a temperature of about 80° C. to 120° C. using a nickel-containing CSZ-1 zeolite which has been cesium or barium-exchanged. Preferred are catalysts having the following compositions (expressed as mole ratios):
0.81 $Cs_2O$:0.14 $Na_2O$:0.2 NiO:$Al_2O_3$: 5.92$SiO_2$ and 0.33 $Cs_2O$:0.58 BaO:NiO: $Al_2O_3$:5.86 $SiO_2$ and 0.62 BaO:0.26 $Cs_2O$:$Al_2O_3$: 5.96$SiO_2$:2.24 NiO and 0.66 BaO:0.29 $Cs_2O$:$Al_2O_3$:5.96 $SiO_2$:0.78 NiO.

To prepare products having a substantial proportion of linear oligomers, i.e., about 10-20% by weight linear oligomers, it is preferred to use the CSZ-1 cesium or barium exchanged nickel-containing catalysts of this invention. Within this category, preferred catalyst embodiments are cesium exchanged CSZ-1 zeolites having a $Cs^+/Na^+$ mole ratio greater than 0.7, especially a $Cs^+/Na^+$ of at least about 2.0 up to about 6.0, and a cesium content of about 18 to 35% by weight, more preferably about 25 to 30% by weight. Barium exchanged catalysts in this preferred category will have a Ba/Cs mole ratio of at least 1 and up to about 2.5.

When it is desired to prepare highly branched products as a result of the oligomerization process of this invention, then either the nickel-containing ELZ-20 or ELZ-omega-5 zeolite catalysts should be used. Typically, these catalysts will provide products containing less than about 2 wt. % of linear oligomers.

Prior to use the catalysts of this invention are vacuum calcined at temperatures of about 375° C. to 475° C. Somewhat lower calcination temperature, i.e., about 275° C. may also be suitable, but generally lower conversions have resulted.

Relative to the amount of olefin, there is employed generally about 10 to 20% by weight of the nickel-containing catalyst of this invention.

The invention is further illustrated by the following examples which are not to be considered as limitative of its scope. (Percentages reported are by weight, except where otherwise indicated.)

CATALYST COMPOSITIONS—EXAMPLES 1–11

EXAMPLE 1

A sample of CSZ-1 was synthesized from a gel having a composition (mole ratios) of 0.5 $Cs_2O$:3.5 $Na_2O$:$Al_2O_3$:
12.5 $SiO_2$:187 $H_2O$, using the general method of U.S. Pat. No. 4,309,313. The product had a chemical composition 0.6 $Na_2O$:0.4 $Cs_2O$:$Al_2O_3$:5.9 $SiO_2$. Twenty grams of this material was exchanged with a solution of 40 g. CsCl in 160 g. water for one hour at room temperature, filtered, then washed with 800 g. water on the filter. The sample was dried at 100° C., then $Ni^{++}$-exchanged in a solution of 8.8 g. $NiCl_2.7H_2O$ dissolved in 160 g. 29% aqueous ammonia solution for 1 hour at room temperature. The sample was vacuum filtered (not washed) and dried at 110° C. for 16 hours. The composition of this final catalyst was: 0.81 $Cs_2O$:0.14 $Na_2O$:0.2 $NiO$:$Al_2$5.92 $SiO_2$, i.e., 1.65% Ni. The catalyst was calcinated at 375° C., under vacuum, for 2 hours before use.

EXAMPLE 2

CSZ-1 was made in a similar manner to that in Example 1, but having a chemical composition of 0.41 $Cs_2O$:0.59 $Na_2O$:$Al_2O_3$:5.92 $SiO_2$. 190 g. was added to 2350 ml. of a 5% solution of $Ba(OH)_2$ pre-adjusted to a pH of 7 with conc. $HNO_3$, and barium-exchanged at 60° C. for 1 hour. After filtering, the barium-exchange was repeated, the product filtered, then washed with 5 l. water and dried at 110° C. A duplicate sample was made in a similar manner. Both samples were combined, placed in a muffle furnace at room temperature and slowly heated to 350° C., then held there for one hour. The hot powder was placed in a Hobart Mixer, and slowly stirred while adding a solution of 155 g. $Ni(NO_3)_2.6H_2O$ dissolved in 485 g. water. The catalyst was air-dried at room temperature for 16 hours, followed by a similar period at 100° C. Chemical analysis gave a composition of 0.33 $Cs_2O$:0.58 $BaO$:$NiO$:$Al_2O_3$: 5.86 $SiO_2$. The catalyst was calcined at 375° C., under vacuum, for 2 hours before use.

EXAMPLE 3

The CSZ-1 zeolite of Example 2 was double $Ba^{++}$ exchanged at 80° C. (100 g. CSZ-1 in 1 l $H_2O$ + 65 g. $Ba(NO_3)_2$), followed by calcination at 110° C. for 3 hours and 350° C. for 2 hours. Half of this Ba-CSZ-1 was impregnated with a solution of 45 g. $Ni(NO_3)_2.6H_2O$ in 90 g. of water, followed by air-drying overnight. Chemical analysis gave a composition of 0.62 $BaO$:0.26 $Cs_2O$:$Al_2O_3$:5.96 $SiO_2$:2.24 NiO. The sample was vacuum calcined at 375° C. for 2 hours before use.

EXAMPLE 4

The second half of the Ba-CSZ-1 described in Example 3 was impregnated with a solution of 15 g. $Ni(NO_3)_2.6H_2O$ dissolved in 90 g. of $H_2O$, then calcined as in Example 3. Chemical analysis of this sample gave 0.66 $BaO$:0.29 $Cs_2O$:$Al_2O_3$:5.96 $SiO_2$:0.78 NiO. The sample was vacuum calcined at 375° C. before use.

EXAMPLE 5

The catalyst was prepared as in Example 2, but the final calcination temperature was 475° C.

EXAMPLE 6

A steamed ultra stable faujasite (ELZ-20, 100 g.), having an Si/Al ratio of 2.7 was heated at 90° C. in 500 g. 2N HCl for 3 hours to remove detrital alumina, filtered and washed with 500 g. water. After drying at 100° C. and rehydrating, the material was steamed in a covered dish at 1500° C. for 20 minutes to further dealuminate the zeolite framework. The product was again acid washed to remove detrital alumina (2 hrs/2N HCl/90° C.), filtered and washed on the filter, first with 300 ml. 1N HCl, then with sufficient water to remove all chloride ion, as demonstrated by testing the filtrate with $Ba(NO_3)_2$ solution. After drying at 100° C., the sample had very good retention of x-ray crystallinity. Ten grams of this high silica faujasite was $K^+$ exchanged (10 g. KCl + 80 g. $H_2O$) for 1 hour at 60° C., filtered, washed with water, then exchanged with 4.4 g. $NiCl_2.7H_2O$ in 80 g. $H_2O$ for 1 hour at room temperature. After filtering, the sample was dried at 110° C. Chemical analysis using an IC plasma spectrometer gave values of 30.9 Si, 1.31% Al, 0.895% Ni and <0.01% Na, representing Si/Al=22.6 and Ni/Al=0.31.

EXAMPLE 7

A sample of high silica faujasite was made as described in Example 6, but not exchanged with $Ni^{++}$.

EXAMPLE 8

A 200 g. sample of ammonium exchanged zeolite omega (ELZ-omega-5), having an Si/Al ratio of 4.3, was exchanged with 2 l. 10% ammonium sulfate solution for 1 hour at room temperature. After filtering, it was washed with 4 l. of $H_2O$, then air dried 16 hours at room temperature. It was then exchanged with a solution of 50 g. $Ni(NO_3)_2.6H_2O$ in 1200 g. $H_2O$ for 1 hour at room temperature. After filtering and washing it was dried at 110° C. Chemical analysis gave 29.8% Si, 7.28% Al, 0.82% Ni, 0.07% Na.

EXAMPLE 9

A sample of the omega-5 was ammonia exchanged as in Example 8. It was not exchanged further with $Ni^{++}$.

EXAMPLE 10

A sample of ELZ-omega-5 (20 g.) was exchanged with a solution of 20 g. $NH_4Cl$ in 200 g. $H_2O$ for 1 hour at room temperature, filtered, washed with 1 l. H$_2$O, then dried at 100° C. It was then exchanged with a solution of 5 g. Ni(NO$_3$)$_2$.6H$_2$O in 120 g. H$_2$O for 1 hour at room temperature, filtered, washed and dried. Chemical analysis gave a composition of 29.84% Si, 7.00% Al, 0.06% Na, 0.87% Ni.

EXAMPLE 11

A sample of CSZ-1 having an approximate composition 0.4 Cs$_2$O:0.6 Na$_2$O:Al$_2$O$_3$:5.26 SiO$_2$ was made using the method of U.S. Pat. No. 4,309,303. 20 g. was exchanged with ammonium, then nickel, in the same manner as Example 1. Chemical analysis gave a composition of 21.02% Si, 8.20% Al, 0.34% Na, 2.26% Ni.

OLIGOMERIZATIONS—EXAMPLES 12–42

General Procedure

A 300 ml. Hoke pressure vessel was fitted with an internal thermocouple at one end and an 1800 psi safety disk and valve at the other end. The valve and safety disk were connected for easy removal. The solid catalyst was charged by detaching the valve and safety disk, then adding the catalyst through the resulting opening.

The olefin was added as a liquid. The Hoke vessel was closed, evacuated and attached to a second vessel charged with a measured amount of liquid propylene or butene. The connecting valve was opened, whereby the liquid was transferred into the reaction vessel.

The vessel was placed on a mechanical shaker and heated at the designated temperature while shaking. After the completion of the test, the vessel and contents were cooled and slowly vented of unreacted monomeric olefin. The contents were removed and weighed.

For analysis, the product was diluted with heptane and analyzed by gas chromatographic techniques to obtain the monomer-dimer-trimer-tetramer composition. It was then hydrogenated in a Parr apparatus, under 60 psi H$_2$/60° C., over 0.5% pt. on Al$_2$O$_3$ catalyst for 4 hours. Re-analysis by gas chromatograph allowed a determination of the dimer skeletal structure by comparison of retention times with known isomers.

EXAMPLE 12

The Ni/Ba/CSZ-1 catalyst described in Example 2, 12.05 g., was charged into the Hoke reaction vessel. Then 82.5 gms. 1-butene was added and the reaction conducted at 110° C. for 15 minutes. Analysis showed that 50.7% of the butene-1 had been converted to oligomers, of which 72.4% was C$_8$, 21.6% was C$_{12}$ and 5.6% was C$_{16}$. The C$_8$ component analyzed after hydrogenation 15.9% linear octane, 52.2% 3-methylheptane and 27.4% 3,4-dimethylhexane. The rate corresponds to 177 moles of olefin converted per mole of nickel per hour (TON). The residual butene was only 3.8% butene-1, indicating a facile concomitant isomerization of 1-butene.

EXAMPLE 13

The reaction was conducted as in Example 12, except for a reaction time of 2.5 hours. The corresponding values from product analyses were:
Conversion, 66.7%
Composition, 65.8% octenes,
    15.5% linear
    47.4% monomethyl-C$_7$
    29.1% dimethyl-C$_6$
25.5% dodecenes
6.8% hexadecenes

EXAMPLE 14

Example 12 was repeated with a reaction time of 4.5 hours. The corresponding values from product analyses were:
Conversion, 69.8%
Composition,
    64.3% octenes,
        15.3% linear
        46.6% methyl-C$_7$
        29.3% dimethyl-C$_6$
    27.1% dodecenes
    7.8% hexadecenes Examples 12–14 demonstrate the rapid conversion to a maximum value of 70%, beyond which no further reaction occurs.

EXAMPLE 15

The procedure of Example 12 was followed with 12.05 g. of the catalyst described in Example 3 being used with 83.8 g. of butene. The reaction temperature was 80° C., the heating period 6.0 hours. The values from product analyses were:
Conversion, 64.0%
Composition,
    67.2% octenes,
        15.2% linear
        49.2% methyl-C$_7$
        29.9% dimethyl-C$_6$
    25.1% dodecenes
    6.1% hexadecenes

EXAMPLE 16

Example 15 was repeated with a reaction temperature of 120° C. and a reaction time of 1.5 hours. The values from product analyses were:
Conversion, 65.3%
Composition,
    64.6% octenes,
        14.4% linear
        41.2% methyl-C$_7$
        32.7% dimethyl-C$_6$
        11.8% other isomers formed by skeletal rearrangements at the higher temperature.
    26.8% dodecenes
    6.8% hexadecenes

EXAMPLE 17

The procedure of Example 12 was followed with 12.0 g. of the catalyst described in Example 4 and 79.6 g. of 1-butene. The reaction temperature was 120° C., held there for 1.5 hours. The values from product analyses were:
Conversion, 65.4%
Composition,
    66.6% octenes,
        13.9% linear
        43.2% methyl-C$_7$
        31.5% dimethyl-C$_6$
        11.5% others
    25.7% dodecenes
    7.1% hexadecenes

EXAMPLE 18

Example 17 was repeated with a reaction temperature of 80° C., time 6.0 hours. The values from product analyses were:
Conversion, 63.7%
Composition,
 69.0% octenes,
  14.2% linear
  50.8% methyl-$C_7$
  29.3% dimethyl-$C_6$
 23.8% dodecenes
 6.5% hexadecenes Examples 12–18 demonstrate that a wide variety of $Ni^{++}$ and $Ba^{++}$ loadings on CSZ-1 zeolite can be tolerated without substantial alteration of conversion and selectivity. Temperatures likewise can be varied with little effect on ultimate conversion, although selectivities may change slightly at the higher end of the range.

EXAMPLES 19–22

The procedure of Example 12 was followed with 12.0 gms of the catalyst described in Example 3 and 81–86 gms of 2-butene. The reaction temperature was 110° C. The reaction times were 0.75, 2.5, 5.5 and 10.0 hours for the following Examples 19–22, respectively. The results are tabulated below. The results show the major components formed; the final three columns show the isomeric distribution of the $C_8$ products.

| Example | Conversion, % | $C_8$, % | $C_{12}$, % | $C_{16}$, % | Linear $C_8$, % | Me-$C_7$, % | Me2-$C_6$, % |
|---|---|---|---|---|---|---|---|
| 19 | 57.3 | 70.0 | 22.3 | 6.0 | 12.3 | 49.8 | 31.7 |
| 20 | 65.2 | 67.9 | 23.8 | 6.6 | 12.5 | 48.1 | 31.6 |
| 21 | 68.3 | 65.9 | 25.4 | 7.0 | 12.8 | 46.9 | 32.0 |
| 22 | 69.9 | 65.6 | 25.7 | 7.0 | 12.8 | 45.8 | 32.3 |

These examples demonstrate that 2-butene also reacts rapidly to give essentially the same results as 1-butene. Analysis of the unreacted butenes from Example 19 showed 3.9% 1-butene. This is the same as that obtained in Example 12, equilibrium of isomers is reached very rapidly. The TON of Example 19 was 34.3 moles of butene converted per hour per mole of nickel.

EXAMPLE 23

The catalyst for this example was prepared as in Example 5. The oligomerization was conducted as in Example 17. The values obtained from product analyses were:
Conversion, 68.8%
Composition,
 62.8% octenes,
  15.1% linear
  41.4% methyl-$C_7$
  32.2% dimethyl-$C_6$
  11.4% others
 27.9% dodecenes
 7.6% hexadecenes

EXAMPLE 24

The catalyst for this example was also calcined at 475° C. The oligomerization was conducted as in Example 18. The values from analyses were:
Conversion, 68.9%
Composition,
 63.7% octenes,
  16.6% linear
  50.4% methyl-$C_7$
  30.5% dimethyl-$C_6$
 27.1% dodecenes
 7.5% hexadecenes Examples 23 and 24 demonstrate that a calcining temperature of 475° C. is equivalent to, but no better than, calcining at 375° C.

EXAMPLE 25

The catalyst for this example was prepared as in Example 2, but was calcined at 275° C. under vacuum. The oligomerization was conducted as in Example 18. The values from analyses were:
Conversion, 32.5%
Composition,
 79.5% octenes,
  18.1% linear
  52.0% methyl-$C_7$
  28.0% dimethyl-$C_6$
 17.9% dodecenes
 2.6% hexadecenes

EXAMPLE 26

The catalyst was that of Example 25. The oligomerization was conducted as in Example 17. The product analyses were:
Conversion, 29.7%
Composition,
 81.3% octenes,
  18.4% linear
  51.1% methyl-$C_7$
  27.1% dimethyl-$C_6$
 16.3% dodecenes
 2.5% hexadecenes

EXAMPLE 27

Example 26 was repeated, except the reaction time at 120° C. was 6.0 hours. The product analyses were:
Conversion, 35.4%
Composition,
 79.5% octenes,
  16.7% linear
  51.1% methyl-$C_7$
  28.6% dimethyl-$C_6$ Examples 25–27 show that a calcination temperature of only 275° C. is very deleterious to the ultimate conversion obtainable. This low conversion is not improved by higher reaction temperature and/or longer reaction time.

EXAMPLE 28 (Comparative)

The catalyst was nickel oxide supported on 75% $SiO_2$/25% $Al_2O_3$ and contained approximately 20% nickel. It was calcined at 500° C. and protected from air and moisture before use. This catalyst (2.5 g., 8.5 m.mole Ni) and 80.6 g. of 1-butene were heated at 91° C. for 1.0 hour with shaking. Recovery and analysis of the product indicated a conversion of 10.4%, for a TON of 17.6 moles per hour. Also, the unreactive butene was 45% 1-butene, which indicated a relatively slow isomerization.

EXAMPLE 29 (Comparative)

Example 28 was repeated with 5.4 g. catalyst (18.4 m.mole Ni) and a 3.0 hours reaction time. The conversion was 39.0% with a TON of 10.1 moles per mole Ni per hour.

EXAMPLE 30 (Comparative)

Example 28 was repeated with 10.0 g. catalyst (34.1 m.mole Ni) and a 5.0 hours reaction time. The conversion was 58.2% and the product composition was analyzed as follows:
61.8% octenes, 14.7% linear
38.1% methyl-$C_7$
47.2% dimethyl-$C_6$

EXAMPLE 31 (Comparative)

Example 28 was repeated with 10.6 g. catalyst (36,1 m.mole Ni), 5.0 hours reaction time and 2-butene as the olefin. The product analyses were:
Conversion, 55.4% (TON, 4.4)
Composition,
67.3% octenes,
7.7% linear
45.2% methyl-$C_7$
45.4% dimethyl-$C_6$ Examples 28–31 show that the the well-known supported nickel-on-silica/alumina catalysts are much less active than the zeolite-based catalysts of this invention. In addition, the zeolite-based catalyst produced 50% more linear octenes from butene-2.

EXAMPLE 32

The catalyst prepared in Example 2, 12.05 g., was charged into the 300 ml. Hoke vessel, then a mixture of 77.1 g. 1-butene and 34.1 g. propylene was charged. The mixture was heated to 80° C. for 5.5 hours. After venting unreacted oleifn, the product weighed 91.4 g. and analyzed as follows:
Hexenes 9.0%
39.7% linear hexenes
51.7% 2-methylpentenes
8.7% dimethylbutenes
Heptenes 22.3%
Octenes 23.4%
15.2% linear octenes
54.0% 3-methylheptenes
30.8% 3,4-dimethylhexenes
Nonenes 15.7%
$C_{10}+$ 28.3%

EXAMPLE 33

Example 32 was repeated with 4.4 g. catalyst, 76.3 g. 1-butene and 76.5 g. propylene. The reaction was run at 654° C. for 2.0 hours. The product weighed 51.3 g. and analyzed as follows:
Hexenes 38.1%
24.6% linear hexenes
68.0% 2-methylpentenes
7.3% dimethylbutenes
31.3% Heptenes
25.4% linear
17.1% Octenes
23.4% linear octenes
48.5% 3-methylheptenes
18.5% 3,4-dimethylhexenes
13.5% $C_9+$ Examples 32 and 33 demonstrate that a mixture of olefins can be employed for co-oligomerization, that the composition can be varied by varying the ratio of olefins in the reacting mixture, and that products with high linear content can be produced.

EXAMPLE 34

The catalyst described in Example 2 was calcined at 375° C. under vacuum for two hours. This catalyst, 7.5 g., was charged into the 300 cc Hoke vessel, then 96.1 g. propylene was charged. The vessel and contents were heated at 90° C. for two hours with shaking. An initial exotherm to 103° C. occurred, which indicated a high catalyst activity. The contents were discharged and hydrogenated for analysis. The results indicated:
Conversion, 73.4%
Composition,
58.5% hexenes,
30.7% linear
62.1% 2-methylpentenes
6.4% 2,3-dimethylbutenes
22.5% nonenes
11.6% dodecenes
2.7% pentadecenes

EXAMPLE 35

The catalyst described in Example 2 was calcined at 375° C. for 2 hours under vacuum. A sample, 6.1 g., was charged to the 300 cc Hoke vessel, followed by 81.1 g. propylene. The vessel and contents were heated to 70° C. with shaking for 1.33 hours. Work-up in the usual manner gave the following analytical results:
Conversion, 70.9%
Composition,
55.1% hexenes,
29.2% linear
63.6% 2-methylpentenes
7.1% 2,3-dimethylbutenes
29.8% nonenes
9.5% dodecenes
2.5% pentadecenes Examples 34 and 35 indicate that the catalyst is very active for the oligomerization of propylene.

EXAMPLE 36

The catalyst for this oligomerization, 7.0 g., was that described in Example 1 which was subsequently calcined at 375° C. for 2 hours under vacuum. After charging the Hoke vessel with this catalyst, 84.8 g. of 1-butene was added and the vessel sealed. The vessel and contents were heated at 120° C., with shaking, for 3 hours. The product was removed and prepared for analysis in the usual manner. Analyses indicated the following:
Conversion, 61.7%
Composition,
61.1% octenes,
15.4% linear
27.5% methyl-$C_7$
42.7% dimethyl-$C_6$
31.6% dodecenes
6.2% hexadecenes The unreacted butene was a mixture of 5.1% 1-butene and 94.9% 2-butene.

This example shows the effectiveness of a cesiumexchanged CSZ-1 catalyst as a support for nickel-catalyzed oligomerization of butenes.

EXAMPLE 37

The catalyst described in Example 6 was calcined at 275° C. A sample, 5.7 g., was heated with 83.8 g. 1-butene at 91° C. for 5 hours. Analysis of the product, after hydrogenation, indicated the following:
Conversion, 68.7%
Composition,
  58.7% octenes,
    1.0% linear
    5.7% methyl-$C_7$
    77.7% dimethyl-$C_6$
    15.5% others
  31.1% dodecenes
  8.4% hexadecenes

EXAMPLE 38

The catalyst described in Example 7 was calcined at 275° C. under vacuum for 2 hours. A portion 4.9 g., was charged to a 300 ml. Hoke vessel, followed by 82.0 g. of 1-butene. The mixture was heated with shaking at 91° C. for 5 hours. Analyses indicated the following:
Conversion, 64.8%
Composition,
  52.4% octenes,
    0.2% linear
    6.5% methyl-$C_6$
    76.3% dimethyl-$C_6$
    17.0% others
  35.1% dodecenes
  9.3% hexadecenes Examples 37 and 38 indicate that the acidic high-silica faujasites produce highly-branched products, even when nickel is present.

EXAMPLE 39

The catalyst described in Example 8 was calcined at 275° C. for 2 hours under vacuum. A sample of this catalyst, 11.8 g., was charged into the 300 cc Hoke vessel in the dry box. After addition of 82.6 g. of 1-butene, the vessel and contents were heated at 91° C. for 5 hours. The product was removed, vented of unreacted butenes (5.0% 1-butene) and analyzed after hydrogenation. The results were:
Conversion, 88.0%
Composition,
  58.5% octenes,
    0.5% linear
    3.0% methyl-$C_7$
    71.1% dimethyl-$C_6$
    25.4% others
  33.2% dodecenes
  7.3% hexadecenes

EXAMPLE 40

Example 39 was repeated with the nickel-free catalyst described in Example 9. Analysis indicated the following:
Conversion, 66.6%
Composition,
  60.5% octenes,
    0.1% linear
    5.5% methyl-$C_7$
    77.2% dimethyl-$C_6$
    17.2% others
  32.4% dodecenes
  6.1% hexadecenes Examples 39 and 40 show the effectiveness of the omega zeolite for selective oligomerizing butenes to highly branched products. The catalyst containing nickel produced higher conversion, with retention of the high selectivity to branched products.

EXAMPLE 41

The catalyst described in Example 10 was calcined at 275° C. under vacuum for two hours. A portion of this catalyst, 11.6 g., was utilized for oligomerizing 81.5 g. of 1-butene at 130° C. for 5 hours. Analyses of the resulting product showed the following results:
Conversion, 98.4%
Composition,
  20.4% octenes,
    0.7% linear
    38.0% methyl-$C_7$
    29.9% dimethyl-$C_6$
    31.5% others
  37.9% dodecenes
  27.5% hexadecenes
  14.2% $C_{20}^+$ This example shows that the nickel-omega catalyst, at higher temperatures, produces a high selectivity for long-chain, branched hydrocarbons.

EXAMPLE 42

The catalyst described in Example 11 was calcined at 275° C. for 2 hours under vacuum. A portion, 8.9 g., was used to catalyze the oligomerization of 85.1 g. of 1-butene at 130° C. for 2.5 hours. The product analyzed:
Conversion, 94.1%
Composition,
  28.1% octenes,
    0.7% linear
    28.0% methyl-$C_7$
    48.8% dimethyl-$C_6$
    22.5% others
  36.8% dodecenes
  23.5% hexadecenes
  11.6% $C_{20}^+$

What is claimed is:

1. A process for oligomerizing $C_3$–$C_{12}$ olefins which comprises contacting a $C_3$–$C_{12}$ olefin or mixtures thereof in the liquid phase at a temperature of about 50° C. to about 150° C. with a calcined nickel-containing zeolite catalyst, the nickel being added in an amount of from about 0.2% to about 20% by weight either by cation exchange or by impregnation, the zeolite being selected from the group consisting of cesium or barium exchanged CSZ-1, high silica ultra-stable faujasites having a $SiO_2$:$Al_2O_3$ ratio of at least about 4.09 and zeolites isostructural with mazzite, the catalyst exhibiting a turnover number of at least 25 moles of olefin per mole of nickel per hour.

2. The process of claim 1 wherein the olefin is propylene or butene-1.

3. The process of claim 1 wherein the catalyst is calcined at a temperature of about 375° C. to about 475° C.

4. The process of claim 1 wherein the catalyst contains from about 1% to about 15% by weight nickel.

5. The process of claim 1 wherein the catalyst is a cesium exchanged CSZ-1 zeolite having a $Cs^+/Na^+$ ratio of from about 2.0 to 6.0, a cesium content of about 18% to 35% by weight and a nickel content of from about 0.2 to about 20% by weight.

6. The process of claim 5 wherein the cesium content is about 25 to 30% by weight and the nickel content is about 1 to 15% by weight.

7. The process of claim 1 wherein the catalyst is a barium exchanged CSZ-1 zeolite having a Ba/Cs ratio of about 1 to about 2.5 and a nickel content of about 0.2 to about 20% by weight.

8. The process of claim 7 wherein the nickel content is about 1% to about 15% by weight.

9. The process of claim 5 or claim 7 wherein the oligomerized olefins contain from about 10 to about 30% by weight linear oligomers.

10. The process of claim 9 wherein the olefin is a $C_3$ or $C_4$ olefin.

11. The process of claim 10 wherein the catalyst is a high silica ultra-stable faujasite.

12. The process of claim 1 wherein the catalyst is zeolite omega.

13. The process of claim 11 or 12 wherein the oligomerized olefins contain less than about 2% by weight linear oligomers.

* * * * *